US00PP37301P2

(12) United States Plant Patent
Trees

(10) Patent No.: US PP37,301 P2
(45) Date of Patent: Mar. 3, 2026

(54) ***BUDDLEJA* PLANT NAMED 'SFF22-062'**

(50) Latin Name: ***Buddleja* x *hybrida***
Varietal Denomination: SFF22-062

(71) Applicant: Sunrise Farm Flowers, LLC, Arroyo Grande, CA (US)

(72) Inventor: Scott C Trees, Arroyo Grande, CA (US)

(73) Assignee: Sunrise Farm Flowers, LLC, Arroyo Grande, CA (US)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 19/048,520

(22) Filed: Feb. 7, 2025

(51) Int. Cl.
*A01H 5/02* (2018.01)
*A01H 6/00* (2018.01)

(52) U.S. Cl.
USPC ..... Plt./242
CPC ..... *A01H 6/00* (2018.05)

(58) Field of Classification Search
USPC ..... Plt./242
CPC ..... A01H 5/02
See application file for complete search history.

(56) References Cited

PUBLICATIONS https://planthaven.com/wp-content/uploads/2024/02/Buddleja-BABY-BUZZ®-Lipstick-Pink-PK.pdf; May 28, 2025; 1 page.*
www.bfgsupply.com/media/10341/2024-2025-psi-product-program.pdf; 2025; 6 pages.*

* cited by examiner

*Primary Examiner* — Kent L Bell
(74) *Attorney, Agent, or Firm* — Weatherly IP Solutions, LLC; James M. Weatherly; Karen P. Bechtold

(57) ABSTRACT

A new cultivar of *Buddleja* named 'SFF22-062' that is distinguishable by its compact pendulous growth habit suitable for use in hanging baskets, with approximately 300 outward-facing flowers, with flowers having intense non-fading pink color and yellow-orange eyes due to that coloration within the central corolla tube and on the petal bases, is disclosed.

2 Drawing Sheets

Genus and species: *Buddleja* x *hybrida*.
Variety denomination: 'SFF22-062'.

BACKGROUND

The present disclosure relates to a new and distinct cultivar of *Buddleja* plant, also known as butterfly bush, a perennial or shrub that is grown for use as an ornamental landscape and container plant and as a hanging basket. The new variety is known botanically as *Buddleja* x *hybrida* and will be referred to hereinafter by the cultivar name 'SFF22-062'.

'SFF22-062' originates from a *Buddleja* breeding program, which was started in 2018 and conducted at the inventor's nursery in Arroyo Grande, California. The aim of the breeding program is to develop a series of compact varieties of *Buddleja* x *hybrida* with pendulous habits especially suitable for use in hanging baskets and planted containers, bearing pendulous flowering inflorescences in a range of colors. The first variety to be released from the breeding program was *Buddleja* Plant named 'SFF21-026' (U.S. Plant Pat. No. 35,795). The inventor has also released *Buddleja* Plant named 'SFF22-053' (co-pending U.S. Plant patent application Ser. No. 19/048,472).

The inventor wished to develop further varieties which are compatible in plant habit with the prior releases as above, but exhibiting different flower colors or color combinations.

The breeding of 'SFF22-062' commenced in fall 2018 with the harvesting of seeds from a *Buddleja* plant known to the inventor as 'SFF-BUD-21-035' (unnamed and unreleased and not patented) which is the open-pollinated female parent variety. The male parent is unknown. The harvested seeds were sown and grown out and evaluated for plant habits in three growing cycles from 2019 to 2022 during which period the inventor evaluated the grown-on seedlings for suitability for use in hanging baskets and compatibility with other releases from the breeding program. The inventor selected 'SFF22-062' in 2022 for its plant habit and characteristics similar to 'SFF21-026' and 'SFF22-053' but with the unique characteristic of its intense lustrous rose-pink colored flowers.

The inventor first asexually propagated 'SFF22-062' in spring 2022 in a greenhouse at the inventor's nursery in Arroyo Grande, California using stem cuttings rooted in inert rooting wedges. The inventor has confirmed that 'SFF22-062' is stable and reproduces true to type in successive generations of asexual reproduction.

SUMMARY

The following traits have been repeatedly observed and represent the distinguishing characteristics of 'SFF22-062'. 'SFF22-062' has not been tested under all possible conditions and phenotypic differences may be observed with variations in environmental, climatic, and cultural conditions, without however, any variance in genotype.

1. 'SFF22-062' exhibits a pendulous growth habit with short internodes suitable for use in hanging baskets.
2. The dimensions of 'SFF22-062' are 30 cm in height and 90 cm in diameter at the end of the first growing season.
3. The stems of 'SFF22-062' arch downwards when laden with flowers (inflorescences).
4. The inflorescences of 'SFF22-062' bear approximately 300 outward-facing flowers.
5. The flowers of 'SFF22-062' are intense non-fading pink in color and exhibit yellow-orange eyes due to that coloration within the central corolla tube and on the petal bases.
6. 'SFF22-062' sets few seeds and remains in bloom for 12 months continually in the Central Coast of California.
7. 'SFF22-062' grows and flowers rapidly. Fully flowering plants may be produced in 1 or 2 gallon containers in 10 to 12 weeks from planting a well-rooted cutting or young plant.

DESCRIPTION OF THE PHOTOGRAPHS

The accompanying color photographs illustrate the overall appearance of the new *Buddleja* cultivar 'SFF22-062' showing the colors as true as it is reasonably possible to obtain in colored reproductions of this type. Photographs were taken in August 2022 in Santa Barbara, California from a one-year-old plant grown outdoors in a 2-gallon container, with one pinch after initial cutting establishment and without any chemical growth regulators. Colors in the photographs may differ from the color values cited in the detailed botanical description, which accurately describes the actual colors of the new variety 'SFF22-062'.

DESCRIPTION OF THE NEW VARIETY

Figure 1:
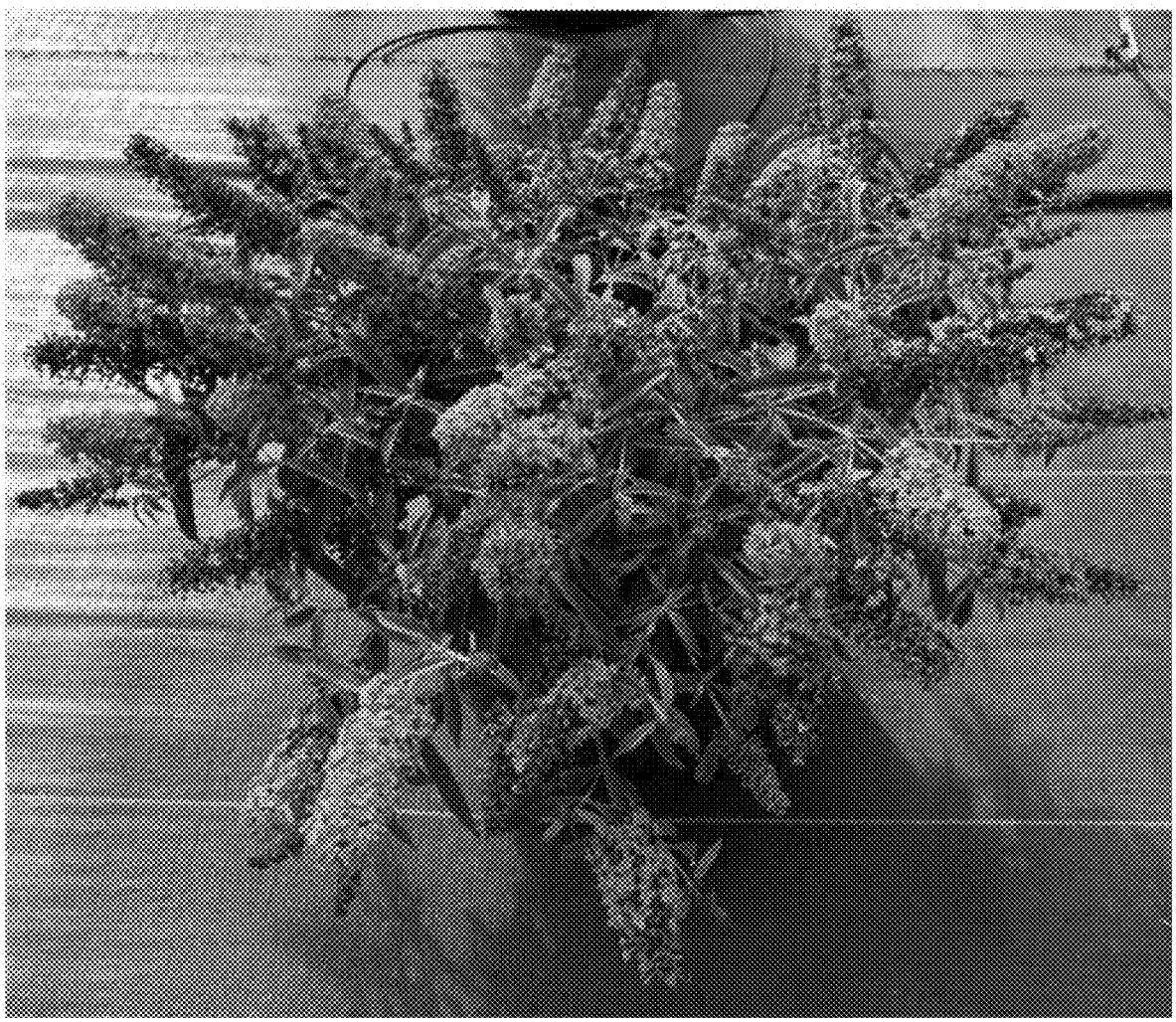
FIG. 1 depicts an entire plant in flower of 'SFF22-062'.
Figure 2:
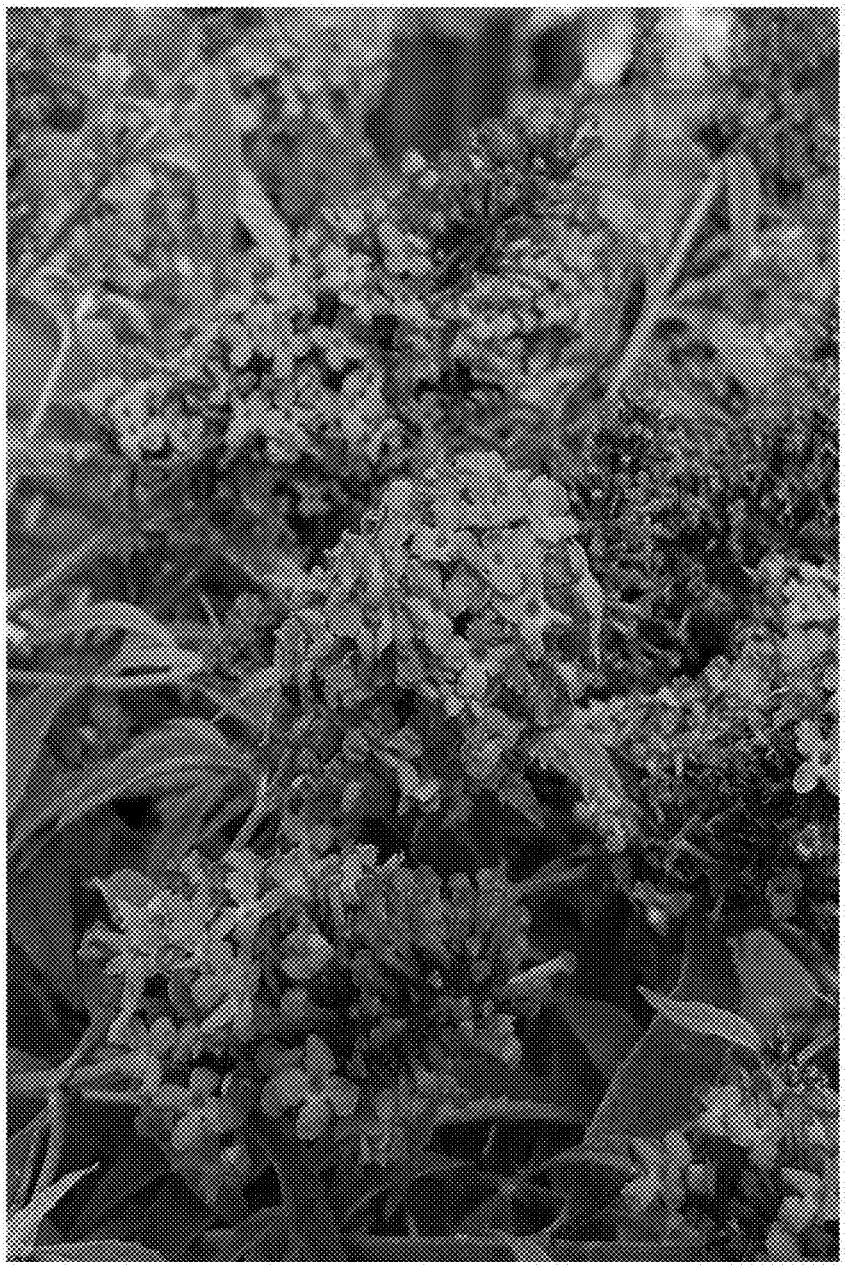
FIG. 2 depicts a close-up view of the inflorescences of 'SFF22-062' showing the panicles of rose-pink flowers with yellow-orange eyes.

The following detailed descriptions set forth the distinctive characteristics of 'SFF22-062'. Observations, measurements, values, and comparisons were collected in August 2024 in Santa Barbara, California from a one year old plant which had been growing outdoors in full sun in a 2-gallon container, with one pinch after initial cutting establishment and without any chemical growth regulators. Color determinations were made in accordance with The 2007 Royal Horticultural Society Colour Chart from London England, except where general color terms of ordinary dictionary significance are used.

Plant:

*Commercial classification.*—Shrub and perennial.

*Common name.*—Butterfly bush.

*Type.*—Ornamental.

*Uses.*—Hanging baskets, container plant for the deck or patio, perennial plant in an herbaceous border or for planting as a shrub in the landscape. Stems and foliage may be used in cut flower arrangements.

*Container size.*—Suggested size is 1-gallon or 2-gallon container, or 8-inch to 10-inch diameter hanging basket.

*Cultural requirements.*—Plant in well-drained soil, position in full sun, and maintain moderate watering. For hanging baskets, pinch out the young growing tip to encourage branching. For use in the landscape, prune branches hard back in spring to 7.5 cm to 10.0 cm in length.

*Blooming seasons.*—Continually in bloom year-round in central coast California.

*Vigor.*—Rapid growth rate. Plant will fill out and flower in a 1 gallon contain in 12 to 14 weeks from planting a rooted cutting.

*Plant habit.*—Prostrate, flowering stems arching downwards.

*Dimensions after first season of growth.*—30 cm in height, 90 cm in width.

*Hardiness.*—Evergreen in USDA Hardiness Zone 8 and warmer, semi-evergreen in USDA Hardiness Zone 7, and deciduous in USDA Hardiness Zone 7 and colder.

*Heat and humidity tolerance.*—Performs well in hot humid conditions.

*Drought tolerance.*—High.

*Pest and disease susceptibility.*—None.

Botanical classification:

*Genus.*—*Buddleja.*

*Species.*—X *hybrida.*

*Denomination.*—'SFF22-062'.

Parentage: 'SFF22-062' is a hybrid that resulted from the open pollination of the following parent plants:

*Female parent.*—*Buddleja* 'SFF-BUD-21-035' (unnamed and unreleased proprietary seedling).

*Male parent.*—Unknown variety.

Propagation:

*Propagation.*—Softwood cuttings taken above or below the node.

*Rooting.*—Cuttings may be rooted in convention peat-based rooting medium or in inert cells or wedges.

*Root system.*—Fibrous.

*Time to initiate rooting.*—2 to 3 weeks are required to produce a cutting which is viable on its own roots.

*Temperature to initiate rooting.*—Under greenhouse conditions, 20° Centigrade.

*Crop time.*—From planting and pinching (stopping) a well-rooted cutting or young plant, 10 to 12 weeks are needed to produce a full and flowering 1-gallon or 2-gallon container.

*Special growing requirements.*—For a long-term landscape planting, prune stems back to 7.5 cm to 10.0 cm in length in early spring of each year.

Base (trunk): A trunk is formed beneath the first pinch or pruning.

*Trunk height.*—Determined by height of first pruning, recommended between 5 cm and 10 cm above ground or soil level.

*Trunk surface.*—Woody, bark fibrous and fissured.

*Basal stem color.*—197B.

Branches, lateral stems:

*Description.*—Plant is strongly apically dominant, sending up branches around the base and apex of the trunk and occasionally from underground. These basal stems grow rapidly and bear terminal paniculate inflorescences. Lateral stems begin to develop and flower as the basal stems begin to flower. Secondary stems are relatively short and only develop once the inflorescences on the basal stems have finished flowering.

*Basal stems.*—Shape: Square with rounded edges. Length: 30.0 cm to 35.0 cm from base to base of inflorescence, 45.0 cm to 50.0 cm in length including the inflorescence. Width: 5 mm at stem base, 4 mm immediately below inflorescence. Surface texture: Puberulent, appears downy. Color: 202C. Internode distance: Varies between 5.0 cm and 6.0 cm. Basal stem strength: Moderately stiff and wiry.

*Secondary (lateral) stems.*—Quantity: 6 to 8 in pairs at each lower basal stem node. Dimensions: Length up to 10 cm, diameter up to 2.0 mm, internode distance 2.5 cm to 3.5 cm. Color: 198D except uppermost internode darker 202C. Surface: Puberulent, downy, hairs approximately 0.5 mm to 1.0 mm in length, color 192C, except uppermost internode glabrous, color 202C.

Foliage:

*Type.*—Evergreen in hardiness zone 8.

*Leaf arrangement.*—Opposite.

*Leaf division.*—Simple.

*Leaf quantity.*—8 to 10 leaves per basal stem, 2 to 6 leaves per secondary stem.

*Leaf shape.*—Narrow lanceolate.

*Leaf base.*—Attenuate.

*Leaf apex.*—Acute.

*Leaf dimensions.*—Up to 8.5 cm in length, 1.75 cm to 2.0 cm in width.

*Leaf color (adaxial surface).*—143C.

*Leaf color (abaxial surface).*—141D.

*Leaf surface (both).*—Lightly puberulent.

*Leaf margins.*—Dentate, approximately 18 teeth per leaf edge, approximately 2 to 3 teeth per cm. Tooth depth 1.0 mm. Teeth angled towards leaf apex.

*Leaf venation.*—Pinnate, slightly depressed on adaxial surface, midrib depressed and appearing as a longitudinal fold in the leaf.

*Vein color (adaxial surface).*—As leaf except midrib color darker 147B.

*Vein color (abaxial surface).*—145D.

*Leaf attachment.*—Sessile, occasionally very short petiolate.

Petioles (where present):

*Shape.*—Terete.

*Dimensions.*—1.0 mm to 2.0 mm in length, 1.0 mm in diameter.

*Color.*—202C.

*Surface.*—Lightly puberulent.

Peduncle:

*Dimensions.*—7.0 mm in length, 1.0 mm in diameter.

*Shape.*—Terete.

*Surface.*—Lightly puberulent.

*Color.*—202C.

Inflorescence:

*Inflorescence.*—Terminal cymose panicle.

*Dimensions.*—10 cm to 13 cm in length, 5.0 cm to 5.5 cm in width at base.

*Shape.*—Short terete cylindrical, apex rounded in outline, base truncate in outline.

*Lastingness.*—Whole inflorescence bears fresh flowers for 5 to 7 days before flowers senesce from base to apex. Some color remains in each inflorescence for 3 to 4 weeks before aging to dark brown in color and eventually falling away

*Fragrance.*—Pleasantly fragrant, lilac-like.

*Use as cut flower.*—The flowers of the inflorescence lose color and age within 3 to 5 days off the plant. The inflorescence becomes unattractive and is not suitable for use as a cut flower except for very brief periods in informal arrangements.

Pedicel:

*Description.*—Short pedicel subtends one pair of flowers.

*Dimensions.*—2.0 mm to 3.0 mm in length and 0.5 mm in diameter.

*Pedicel shape.*—Terete.

*Pedicel color.*—202C.

*Pedicel surface.*—Lightly puberulent.

Bud:

*Shape.*—Ovoid, tightly enclosed within clasping calyx and sepals.

*Dimensions.*—3.0 mm in length, 2.0 mm in diameter including clasping calyx.

*Color.*—Initially as calyx 183D then opening to reveal petals ranging between N15A and 75C.

*Surface.*—Smooth, rugose.

Flowers:

*Shape.*—Salverform, consisting of slender corolla tube (fused petal bases) and rotate free terminal petal lobes.

*Description.*—Flowers densely arranged in the inflorescence with outward-facing petal lobes whose adaxial surfaces are vibrant rose-pink in color above corolla tube whose inner surface is yellow-orange in color, appearing as a central eye.

*Quantity.*—From 5 to 7 flowers per cyme, approximately 16 cymes per inflorescence. Overall, approximately 350 flowers per inflorescence.

*Dimensions.*—9.0 mm in length including corolla tube, 8.0 mm in diameter (across petal lobe apices).

*Corolla tube.*—Shape: Tubular, irregular diameter ranging between 1.5 cm and 2.0 cm. Dimensions: Tube 6 mm in length, 2 mm in diameter. Surfaces (both): Glabrous and glossy, 1.5 cm to 2 cm in diameter. Color (inner surface): Midway between 17B and 28A. Color (outer surface): 64D.

*Petals (free petal lobes).*—Shape: Rotate with four broad free petal lobes. Apex Shape: Crenate. Margin Type: Smooth, entire, wavy. Dimensions (including lobes): 5.0 mm to 6.0 mm in length, 4.0 mm in width. Lobe dimensions: 4.0 mm in length and width. Lobe shape: Spatulate, base truncate, apex crenate. Lobe margin: Wavy. Surfaces (petals, lobes, both surfaces): Glabrous, lustrous. Color (petal lobes adaxial surfaces): 61D, base midway between 17B and 28A. Color (petal lobes abaxial surface): 62A. Corolla eye (formed from lobe bases): 25C.

Calyx, sepals:

*Description.*—Calyx initially tightly clasps bud as corolla tube grows and extends and flowers open.

*Calyx shape.*—Tubular, consisting of 4 sepals, longitudinally fused at sepal margins which appear as darker calyx ribs.

*Sepals.*—Quantity: 4. Shape: Rectangular, longitudinally incurved to clasp corolla tube. Dimensions: 2.5 cm in length, 0.5 cm in width. Apex: Truncate. Base: Obtuse. Margin: Entire, adjacently fused to form ribs. Surface (both surfaces): Smooth. Color (both surfaces): 183D except margins (ribs) 200A.

Reproductive organs:

*Description.*—Reproductive organs tiny and located within corolla tube.

*Stamens*.—Quantity, arrangement: 4, attached at base of corolla tube and borne entirely within the tube. Filaments: Very short (shorter than anthers) and positioned towards tube base. Filament color: NN155C. Anthers: Approximately 1.0 mm in length and very thin. Positioned at or slightly below tube mouth. Anther color: NN155D. Pollen: None observed.

*Pistil*.—Quantity: 1, style less than 1 mm in length, white, NN155C. Stigma: Not observed.

*Ovary*.—Not observed.

*Seed*.—Quantity: Sparse (low seed set for the genus). Color: 200C.

*Shape*.—Ovoid.

COMPARISON WITH PARENTS AND CLOSEST KNOWN VARIETY

'SFF22-062' may be compared with the female parent variety, *Buddleja* 'SFF-BUD-21-035' as follows: the flower petals and lobes of 'SFF22-062' are lustrous and darker pink in comparison with the flower petals and lobes of 'SFF-BUD-21-035' which are mid rose-pink in color. The flower petals and lobes of 'SFF22-062' are rose-pink in color.

The male parent variety of 'SFF22-062' is unknown: no comparison is possible.

The closest variety of *Buddleja* known to the inventor is the inventor's commercial variety of *Buddleja* Plant named 'SFF21-026' (U.S. Plant Pat. No. 35,795). The flower petals and flower lobes of 'SFF22-062' are lustrous darker pink in color in comparison with lighter colored rose-pink flowers of 'SFF21-026'. In addition, the eyes (i.e. the inner surfaces of the corolla tubes) of the flowers of 'SFF22-062' are lighter and brighter yellow-orange in color whereas the eyes of 'SFF21-026' are darker orange-yellow in color.

I claim:

1. A new and distinct cultivar of *Buddleja* Plant Named 'SFF22-062' as described and illustrated herein.

* * * * *